United States Patent [19]

Byvik et al.

[11] Patent Number: 4,890,915

[45] Date of Patent: Jan. 2, 1990

[54] METHOD AND APPARATUS FOR DETERMINING OPTICAL ABSORPTION AND EMISSION CHARACTERISTICS OF A CRYSTAL OR NON-CRYSTALLINE FIBER

[75] Inventors: Charles E. Byvik, Hampton; A. Martin Buonchristiani, Newport News, both of Va.

[73] Assignee: The United States of America as represented by the Administrator of the National Aeronautics and Space Administration, Washington, D.C.

[21] Appl. No.: 232,735

[22] Filed: Aug. 16, 1988

[51] Int. Cl.⁴ .................. G01N 21/64; G01N 21/84
[52] U.S. Cl. ................................. 356/73; 356/73.1
[58] Field of Search ..................... 356/30, 73, 73.1

[56] References Cited

U.S. PATENT DOCUMENTS

| | | | |
|---|---|---|---|
| 4,556,314 | 12/1985 | Stone | 356/73.1 |
| 4,613,757 | 9/1986 | Deserno et al. | 356/73.1 X |
| 4,657,388 | 4/1987 | Coppa et al. | 356/73.1 |
| 4,659,215 | 4/1987 | Sumida et al. | 356/73.1 |
| 4,662,743 | 5/1987 | Nishimura et al. | 356/73.1 |
| 4,730,922 | 3/1988 | Bach et al. | 356/73 |

*Primary Examiner*—Vincent P. McGraw
*Attorney, Agent, or Firm*—Harold W. Adams; John R. Manning; George F. Helfrich

[57] ABSTRACT

A method of determining optical absorption and emission spectra from a crystal or non-crystalline fiber sample includes directing a laser light source to a side of the fiber sample and measuring fluorescence intensity at various positions along the crystal fiber sample, and then directing a broadband light source through the ends of the crystal fiber sample and measuring absorption in a region of no fluorescence. The preferred apparatus for carrying out the method includes a broadband light source to generate measurable absorption outside the region of fluorescence and a laser light source for generating measurable absorption in the region of fluorescence.

9 Claims, 3 Drawing Sheets

METHOD AND APPARATUS FOR DETERMINING OPTICAL ABSORPTION AND EMISSION CHARACTERISTICS OF A CRYSTAL OR NON-CRYSTALLINE FIBER

ORIGIN OF THE INVENTION

The invention described herein was made in the performance of work under NASA Grant NASw-3458. In accordance with 35 USC 202, the grantee elected not to retain title.

BACKGROUND OF THE INVENTION

1. Field of the Invention

The present invention relates generally to spectroscopy and, more specifically, to a method and apparatus for performing spectroscopic analysis of crystal or non-crystalline fibers.

2. Description of the Related Art

Presently, there is a need to develop new materials for solid state lasers. Research efforts are continuing to identify materials which extend the range of solid state laser wavelengths. It can be expected that many new materials with useful emission wavelengths remain yet to be discovered.

Optical spectroscopy plays an important role in the search for new solid state laser materials since spectroscopic analysis can be used both to characterize new laser materials and to improve their performance by optimizing crystal properties.

Growth of new laser materials in bulk, for example by the Czochralski, flame fusion, or heat exchange methods, is expensive and time consuming. An alternative, more practical method is to form single crystal fibers of the material to be studied. One method for forming crystal fibers is the laser heated pedestal method (LHPE) for the growth of single crystal fibers with diameters ranging from tens of micrometers to millimeters. Basically, the LHPE method results in rapid growth and reduced contamination and stress problems. A $CO_2$ laser is split into two beams which are focused onto the end of a rod of the material to be grown into a fiber. When the fiber starts to grow, a source rod is fed into the laser beam to maintain a constant amount of volume. Typically, the diameter of the fiber is between one-half and one-quarter the diameter of the source rod.

The laser heated pedestal fiber growth process allows surveys for new laser materials as well as optimizing their lasing characteristics to be conducted more rapidly and less costly than conventional growth methods. However, their size and optical quality pose new problems of analysis thereof.

SUMMARY OF THE INVENTION

An object of the present invention is to provide a rapid and inexpensive method and apparatus for determining the absorption and emission characteristics of crystal fibers.

Another object of the invention is to provide a method and apparatus for determining the optical properties of solid state laser materials using single crystal fibers grown by a laser heated pedestal growth method or by any similar technique.

Yet another object of the invention is to provide a simple method and apparatus for extracting the optical absorption and emission spectra of materials in the form of insulating crystal fibers.

Another object of the invention is to provide a method for determining the absorption and emission characteristics of crystal fibers with doped transition metal ions or rare earth ions doped into crystal fibers of any diameter.

In a preferred embodiment of the invention, a method of determining optical absorption and emission spectra for a crystal fiber sample having opposite sides and opposite ends includes the steps of directing a laser light source to a side of the crystal fiber sample at a plurality of positions along the side of the crystal fiber sample, measuring fluorescence intensity emerging from the fiber end at each position along the crystal fiber sample, and from this information the fluorescence intensity corrected for self-absorption can be extracted. Furthermore, by directing a broadband light source through the ends of the crystal fiber sample, the absorption in a region of no fluorescence can be measured.

In another embodiment of the invention, an apparatus for determining optical absorption and emission spectra for a crystal fiber sample having opposite sides and opposite ends polished flat includes a laser light source directed to a side of the crystal fiber sample for inducing fluorescent radiation which is emitted from the ends of the sample, means for measuring the intensity of the laser induced fluorescent radiation, first means for determining absorption and emission spectra in the emission region, a broadband light source directed through an end of the crystal fiber sample, and second means for determining an absorption spectrum outside the emission region, the first and second means providing absorption and emission spectra over an entire spectral region of the sample. The absorption and emission spectra of noncrystalline fibers can be obtained in a similar manner.

These objects, together with other objects and advantages which will be subsequently apparent reside in the details of construction and operation of the apparatus as more fully hereinafter described and claimed, reference being had to the accompanying drawings forming a part hereof, wherein like reference numerals refer to like parts throughout.

DETAILED DESCRIPTION OF THE PREFERRED EMBODIMENTS

In the following description, an example will be referred to in which a crystal fiber sample 14 is a crystal fiber of trivalent titanium doped sapphire ($Ti^{3+}$: $Al_2O_3$). The sapphire fiber used experimentally to demonstrate the present invention was grown with its c-axis oriented 60° with respect to the fiber axis. The fiber was about 1 mm in diameter and about 5 cm long. The parallel end faces were polished as were two planes parallel to the axis of the fiber.

Figure 1:
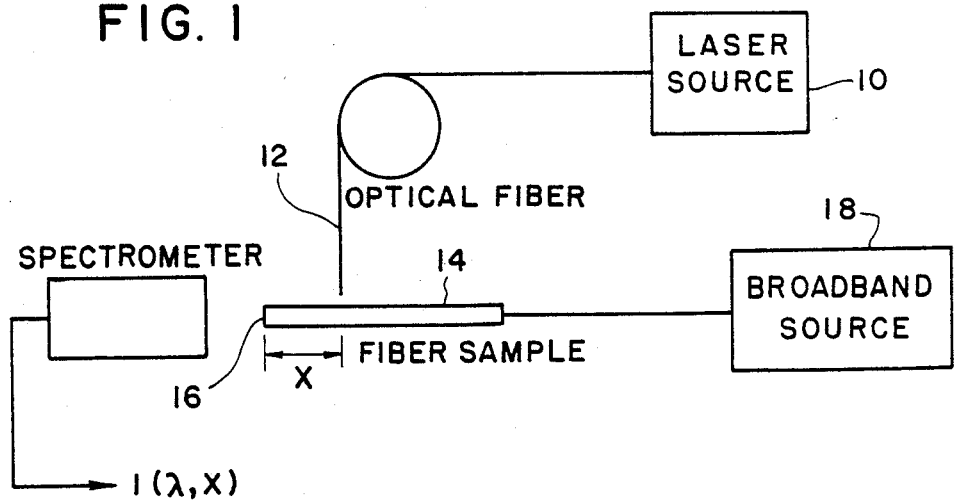
FIG. 1 is a schematic block diagram illustrating a first preferred embodiment of an apparatus according to the present invention.

In the present invention, laser induced fluorescent radiation is analyzed to give both the absorption and fluorescence spectra, after correction for self-absorption, at emission wavelengths. FIG. 1 illustrates an apparatus for analyzing the fluorescent radiation and deriving the absorption and fluorescence spectra. Light from a laser source 10, such as an Argon-ion laser (at a wavelength of about 488 nm), is transported by an optical fiber 12 to a side of the crystal fiber sample 14 to deliver excitation radiation which can be accurately positioned along the side.

The fluorescent emission from the titanium ions is entrained within the crystal fiber sample 14 and exits from the ends 16. The intensity of this radiation depends upon the distance x traveled in the fiber from the point of side introduction to the end of the sample next to a measuring device. The crystal fiber sample is side-excited by the laser light at several points along its length, and the spectral intensity of the emerging radiation is recorded as a function of excitation position. This data is then used to determine the absorption and emission spectra in the emission region according to a formula described below.

Figure 2:
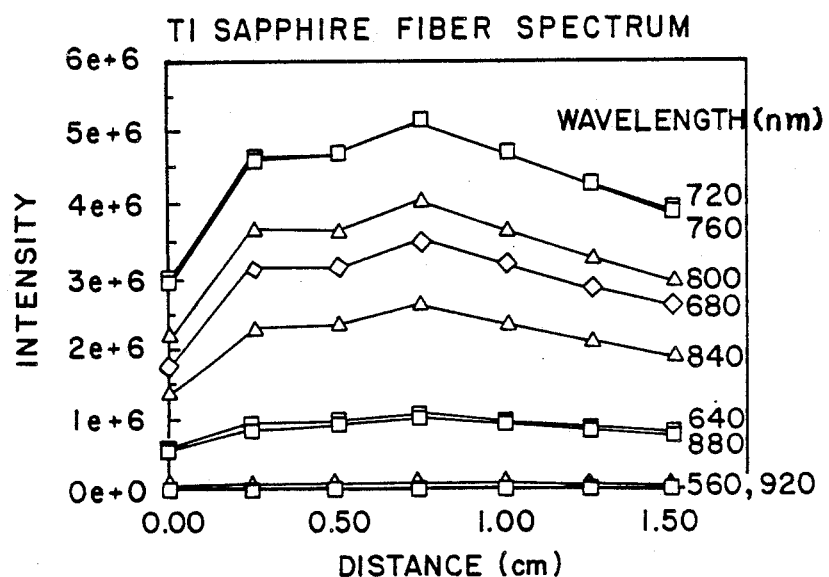
FIG. 2 is a graph showing intensity of fluorescent radiation, at various wavelengths, emerging from the end of a fiber as a function of the distance between the excitation point and the fiber end.

A second measurement is taken and used to determine the absorption spectra away from the emission region by means of a transmission measurement. Light from a broadband source 18 is introduced into one end of the crystal fiber sample 14, and the transmitted radiation is analyzed to derive an absorption spectrum in the wavelength region where there is no fluorescence. The absorption and emission spectra from the two measurements, i.e., using the laser source 10 and the broadband source 18, are combined to give the spectral properties of the sample over the entire spectral region. Typical output at emission wavelengths is shown in FIG. 2, which illustrates test measurements of the laser induced fluorescence intensity emerging from the end of the fiber for several different wavelengths as a function of excitation position.

In FIG. 1, the apparatus may include a lens at opposite ends of the crystal fiber sample 14 to focus the broadband source into the sample fiber. The measurements may be made by a spectrometer 20, or a monochromator.

In analyzing the loss in intensity of the laser induced fluorescence as it passes through the fiber, the present invention distinguishes losses occurring in the fiber bulk from those which occur at the end surface of the fiber. The bulk losses result from absorption and scattering processes within the fiber and thus depend on the distance traveled by the light. The losses occurring at the surface are due to optical discontinuity and are not path dependent. Treating the bulk and surface losses as separate optical elements, the surface elements are characterized by a reflection coefficient, $R_S$, which depends upon the index of refraction of the fiber and is given by the Fresnel formula:

$$R_S = \left| \frac{(N-1)}{(N+1)} \right|^2 \qquad (1)$$

The bulk elements can be treated in terms of distance dependent reflection and transmission coefficients, $R(x)$ and $T(x)$, whose functional form depends on the nature of the radiation transport there. For a more complete explanation of the reflection and transmission coefficients, see "Global Flux Conservation In One Dimensional Transport Processes", by A. M. Buoncristiani and J. Thomchick, *Applied Physics Communication*, 2(3), p. 157–182 (1982-83). In order to demonstrate the measurements required herein, it is sufficient to consider the simplest case where scattering processes are ignored, that is, where $R(x) = 0$ and $T(x) = \exp(-\alpha x)$.

By assuming that the flux into and out of a fiber sample of length, 1, is in a steady-state, the output steady-state flux, I, emerging from the end of a fiber of length, 1, is found to be as follows:

$$I = (1 - R_2) \frac{e^{-\alpha x} + R_s e^{(2L-x)\alpha}}{1 - R_s^2 e^{-2L\alpha}} \frac{I_O}{2} \qquad (2)$$

The spectral distribution of fluorescent radiation emerging from the crystal fiber depends on the excitation position x, the intensity of the induced fluorescence $I_O$ and the two material parameters $R_S$ and $\alpha$. The wavelength dependence of $I_O$, which gives the fluorescence intensity corrected for self-absorption along the crystal fiber and the absorption spectrum $\alpha(\lambda)$ in the wavelength region where there is fluorescence, can be determined by using the data of FIG. 2 and the equations (1) and (2). Thus, by measuring the fluorescent output at several positions x and fitting the measurements into equations (1) and (2) the wavelength dependence of $I_O$ can be determined. This gives the fluorescence intensity corrected for self-absorption along the fiber sample 14 and the absorption spectrum in the wavelength region where there is fluorescence. Basically, the present invention contemplates use of the fluorescent light to measure absorption and to correct the emergent spectrum for the effects of self-absorption. The absorption spectrum in the region where there is no fluorescence is measured directly by a transmission measurement using a broadband source 18.

Figure 3A:
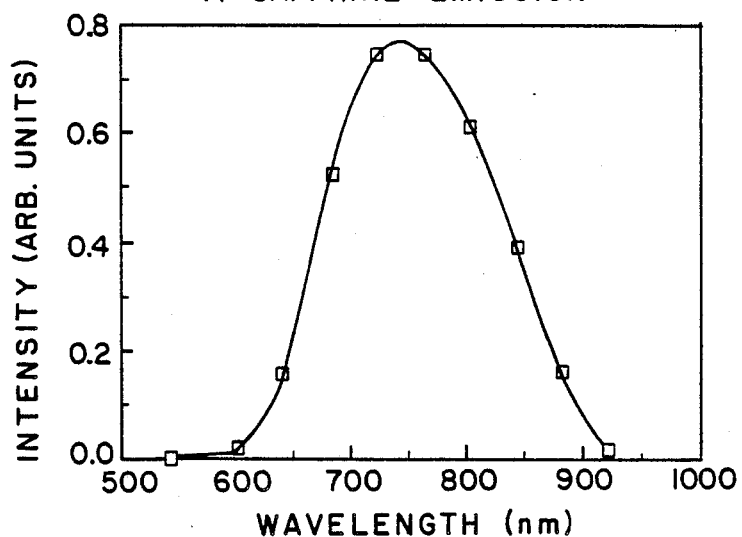
FIGS. 3a and 3b are graphs showing spectral distribution of the fluorescent radiation and absorption for trivalent titanium doped sapphire, as determined from the data in FIG. 2.
Figure 3B:
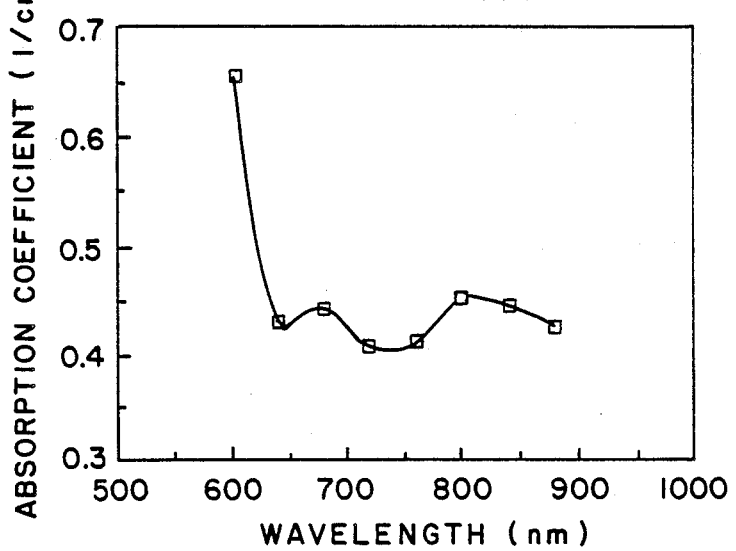

Results of experiments of the intensity as a function of the position of the excitation source, for several wavelengths, are shown in FIG. 2. The amount of light entrained in the crystal fiber and its emergence angle depends upon the position of the exciting light. This effect can be ignored for excitation distances beyond a few fiber diameters from the ends. Fitting the distributions to the formula in equation (2) results in the fluorescent intensity for Ti:Sapphire and the corresponding absorption coefficient shown in FIGS. 3a and 3b. The emission and absorption spectra obtained by this technique are comparable to spectra obtained by more conventional procedures using samples cut and polished from Czochralski grown boules. The fluorescent intensity has proven to be substantially identical to that measured by conventional means.

Figure 4:
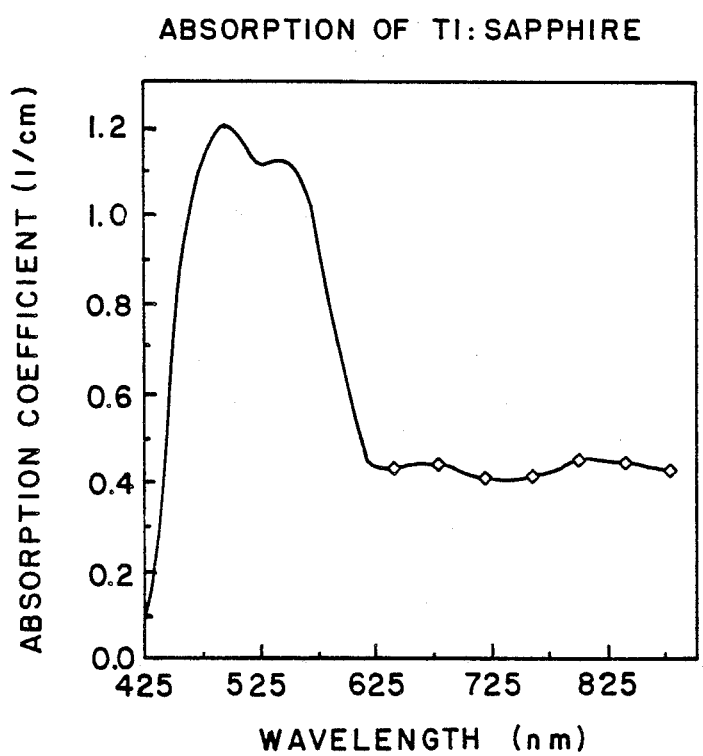
FIG. 4 is a graph showing absorption spectrum of trivalent Titanium doped sapphire determined from laser induced fluorescent (points marked with diamonds) and transmission measurements.

Combining the absorption in the fluorescent region with that obtained from the broadband measurement, one can obtain the complete absorption curve shown in FIG. 4.

According to the present invention, a simple technique for determining the optical absorption and emission spectra for crystal and non-crystalline fiber samples involves taking two direct measurements: fluorescence induced by a laser side-lighting the crystal fiber sample and absorption by direct transmission through the crystal fiber sample. The results of measurements on the fibers compare favorably with measurements on samples grown by more conventional methods.

The many features and advantages of the present invention are apparent from the detailed specification, and thus, it is intended by the appended claims to cover all such features and advantages of the method and apparatus which fall within the true spirit and scope of the invention. Further, since numerous modifications and changes will readily occur to those skilled in the art based upon the disclosure herein, it is not desired to limit the invention to the exact construction and operation illustrated and described. Accordingly, all suitable modifications and equivalents may be resorted to falling within the scope and the spirit of the invention.

What is claimed is:

1. A method of determining optical absorption and emission spectra from a crystal or non-crystalline fiber sample having opposite sides and opposite ends, comprising the steps of:
    measuring fluorescence induced in the crystal or non-crystalline fiber sample by a laser light sidelighting the fiber sample; and
    measuring absorption resulting from a direct transmission of a broadband light transmitting directly through the ends of the fiber.

2. A method according to claim 1, wherein the step of measuring fluorescence induced by a laser light comprises directing a laser light at a point on one of the sides of the crystal or non-crystalline fiber at a predetermined distance from one of the ends thereof to induce fluorescent radiation, a portion of which is emitted from the fiber ends at a level of intensity.

3. A method according to claim 2, further comprising moving the laser light to a plurality of different points along the side of the crystal or noncrystalline fiber and measuring spectral intensity of the emerging radiation as a function of the position of the laser light.

4. A method according to claim 3, further comprising determining absorption and emission spectra in the emission region based on the measured spectral intensity of the emerging radiation.

5. A method according to claim 1, wherein the step of measuring absorption resulting from a direct transmission of a broadband light comprises introducing a broadband light into one of the ends of the crystal or non-crystalline fiber and determining an absorption spectrum in a wavelength region where there is no fluorescence based on transmitted radiation.

6. A method according to claim 5, wherein the absorption and emission spectra from the two measuring steps are combined to give the spectral properties of the crystal or non-crystalline fiber over an entire spectral region.

7. A method of determining optical absorption and emission spectra from a crystal or non-crystalline fiber sample having opposite sides and opposite ends, comprising the steps of:
    directing a laser light source to a side of the crystal or non-crystalline fiber sample at a plurality of positions;
    measuring fluorescence intensity corrected for self-absorption at the plurality of positions along the crystal or non-crystalline fiber sample;
    deriving absorption and emission spectra at emission wavelengths from measured fluorescent intensity;
    directing a broadband light source through the ends of the crystal or non-crystalline fiber sample; and
    measuring broadband induced absorption in a region of no fluorescence.

8. An apparatus for determining optical absorption and emission spectra from a crystal or noncrystalline fiber sample having opposite sides and opposite ends, comprising:
    a laser light source directed to a side of the crystal fiber sample for inducing fluorescent radiation which is emitted from the ends of the sample;
    means for measuring the intensity of the laser induced radiation;
    first means for determining absorption and emission spectra in the emission region;
    a broadband light source directed through an end of the crystal or non-crystalline fiber sample;
    second means for determining an absorption spectrum outside the emission region; and
    the first and second means providing absorption and emission spectra over an entire spectral region of the sample.

9. An apparatus according to claim 8, further comprising means for correcting the measurement of the intensity of the laser induced radiation for self-absorption.

* * * * *